(12) United States Patent
Hopf

(10) Patent No.: US 7,523,563 B2
(45) Date of Patent: Apr. 28, 2009

(54) PROCESS FOR PREPARING CERTAIN HYDROHALIDE METAL COMPLEX COMPOUNDS HAVING A SPECIFIC COARSE STRUCTURE

(75) Inventor: Guenter Hopf, Tutzing (DE)

(73) Assignee: Verla-Pharm Arzneimittelfabrik Apotheker H.J.v. Ehrlich GmbH & Co. KG, Tutzing (DE)

( * ) Notice: Subject to any disclaimer, the term of this patent is extended or adjusted under 35 U.S.C. 154(b) by 431 days.

(21) Appl. No.: 11/206,325

(22) Filed: Aug. 18, 2005

(65) Prior Publication Data

US 2007/0043229 A1    Feb. 22, 2007

(51) Int. Cl.
*F26B 3/00* (2006.01)
*C08B 5/00* (2006.01)
*C07C 57/50* (2006.01)

(52) U.S. Cl. ............................. 34/372; 34/348; 34/363; 427/213; 556/40; 556/41; 562/571; 562/602; 562/840

(58) Field of Classification Search .................. 34/348, 34/363, 372; 427/213; 556/40, 41; 562/400, 562/571, 602, 840, 861
See application file for complete search history.

(56) References Cited

U.S. PATENT DOCUMENTS 4,137,326 A * 1/1979 Fischer et al. ............... 514/561
4,546,195 A * 10/1985 Helbig et al. ................. 556/50

FOREIGN PATENT DOCUMENTS

CA       975376        9/1975
DE    32 38 118 A1    4/1984

* cited by examiner

*Primary Examiner*—H. (Holly) T Le
(74) *Attorney, Agent, or Firm*—Renner, Otto, Boisselle & Sklar, LLP

(57) ABSTRACT

The present invention relates to a process for preparing a granular hydrohalide salt of a particular metal complex compound which is composed of a divalent metal cation as central ion and of an amino dicarboxylic acid ion and, where appropriate, water as ligand, where the hydrohalide salt is obtained with a specific particle size distribution.

11 Claims, 3 Drawing Sheets

PROCESS FOR PREPARING CERTAIN HYDROHALIDE METAL COMPLEX COMPOUNDS HAVING A SPECIFIC COARSE STRUCTURE

The present application claims priority under 35 U.S.C. §119 to prior-filed European Application No. 04 019 858.2, filed 20 Aug. 2004, the disclosure of which is hereby incorporated herein by reference.

BACKGROUND

The present invention relates to a process for preparing a granular hydrohalide salt of a particular metal complex compound which is composed of a divalent metal cation as central ion and of an amino dicarboxylic acid ion and, where appropriate, water as ligand, where the hydrohalide salt is obtained with a specific particle size distribution.

Complexes of a divalent metal cation as central ion and of an amino dicarboxylic acid ligand, and the hydrohalides thereof and various processes for preparing them are known. Complexes of a divalent metal cation as central ion and of an amino dicarboxylic acid ligand, for example magnesium L-aspartate can be handled substantially without problems. In contrast thereto, the hydrohalides thereof, especially magnesium L-aspartate hydrochloride, are usually very hygroscopic, so that they can be prepared only at extremely low humidity. Magnesium L-aspartate hydrochloride liquefies even at a humidity of more than 50 %, making its further processing extremely difficult or even impossible. Further processing to tablets or granules is accordingly possible only in air-conditioned zones with controlled low humidity. Because of the extreme hygroscopicity, it has been possible to date to granulate in particular magnesium L-aspartate hydrochloride only using organic solvents, which is undesired for environmental reasons.

In order to solve the problem of the hygroscopicity of the hydrohalides described above, attempts have been made to prepare a granular product with a reduced total surface area. All attempts made to date to prepare a granular product by spray drying have, however, provided an inadequate, usually very finely powdered material which, because of the large surface area or the high proportion of very finely powdered material, rapidly assumes a honey-like consistency, making further processing impossible. For example, a very finely powdered material is obtained under the spray-drying conditions (air inlet temperature: about 180° C.; air outlet temperature: about 120° C.) indicated in DE 32 38 118 A1 (cf. Examples 1 to 5 of DE 32 38 118 A1).

SUMMARY

The present invention is thus based on the technical object of providing hydrohalides of complex compounds which are composed of a divalent metal cation as central ion and of an amino dicarboxylic acid ion and, where appropriate, water as ligand, and which are intended to have good flow and dissolving properties and reduced hygroscopicity.

This object is achieved by providing the embodiments characterized in the claims.

In particular, a process for preparing a granular hydrohalide of a complex compound which is composed of a divalent metal cation as central ion and of an amino dicarboxylic acid ion and, where appropriate, water as ligand is provided and comprises the steps:

(a) preparation of an aqueous solution of the hydrohalide of the complex compound, (b) spray drying of the aqueous solution obtained in step (a) at an air inlet temperature of from 300 to 350° C. and at an air outlet temperature of from 100 to 140° C. and with a spraying pressure of from 3 to 5 bar.

DETAILED DESCRIPTION

Figure 1:
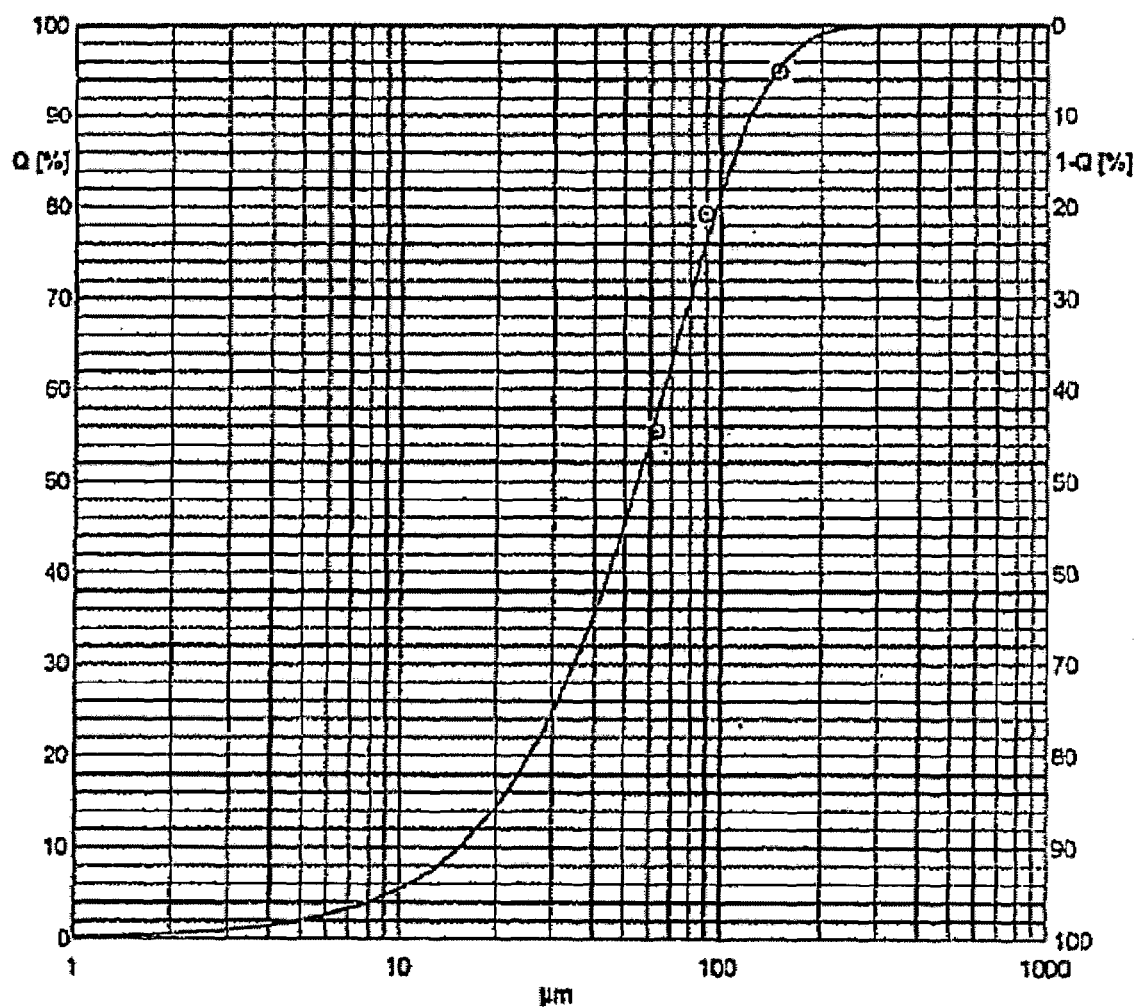
FIG. 1 is a graph showing the particle size distribution of finely powdered magnesium L-aspartate hydrochloride prepared by a standard process disclosed in DE 32 38 118 A1.

The hydrohalides of the complex compounds prepared according to the invention can be prepared in various ways. For example, they can be prepared by mixing equimolar amounts of a metal salt of an amino dicarboxylic acid (with a divalent metal such as, for example, magnesium) and an appropriate metal halide in aqueous solution. However, it is preferred to prepare the hydrohalides of the complex compounds by reacting an amino dicarboxylic acid with a hydroxide, oxide and/or carbonate of the metal (M) in aqueous solution and further reacting the resulting aqueous solution or suspension with a halide of the metal (M) and/or hydrohalic acid. The latter preparation process can start from more favourable and easily available starting compounds, making the overall process more economic.

It is particularly preferred to mix an aqueous solution or suspension of 2 mol of the particular amino dicarboxylic acid with an aqueous solution or suspension of 1 mol of the appropriate metal oxide, hydroxide and/or carbonate and with an aqueous solution or suspension of 1 mol of the appropriate metal halide, and to stir until a clear solution is obtained. Instead of the metal halide it is also possible to use an equimolar amount of a hydrohalic acid and of a metal oxide, hydroxide and/or carbonate. The mixing preferably takes place in a temperature range from about 20 to about 90° C., or in the case of an exothermic reaction at slightly elevated temperature until a clear solution is obtained, which can be purified by filtration. It may be advantageous in some cases firstly to mix the solution or suspension of the amino dicarboxylic acid with the metal oxide, hydroxide or carbonate as solid, solution or suspension and only then, when a clear solution has been obtained, to add the solution of the metal halide.

The hydrohalide of the complex compound is preferably a compound characterized by formula (I) below:

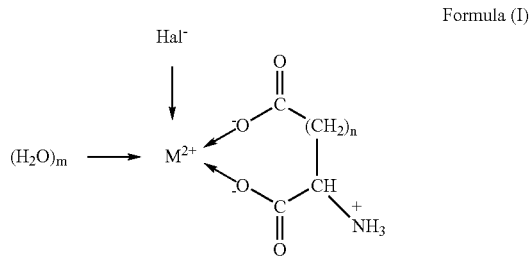

Formula (I)

in which $M^{2+}$ is a divalent metal cation, $Hal^-$ is a halide ion such as fluoride, chloride, bromide or iodide, n is 1 or 2 and m is 0 to 10, preferably 0, 1, 2 or 3.

The amino dicarboxylic acids which can be used are subject to no particular restrictions as long as they are able to form a chelate with a divalent metal cation such as, for example, magnesium, calcium or iron. A skilled person is able to find a large number of suitable substituted or unsubstituted amino dicarboxylic acids able to form a stable complex with a divalent metal cation. It is particularly preferred to use L-glutamic acid or L-aspartic acid as amino-dicarboxylic acid in the process according to the invention.

The metal (M) which is present in the hydrohalide of the complex compound and which represents the central cation of the complex can in principle be any divalent metal cation. The metal (M) is preferably an alkaline earth metal, in particular magnesium, calcium or strontium, or a heavy metal, in particular zinc, iron, manganese, cobalt, copper or cadmium. In the complex obtained according to the invention, the divalent metal cation is complexed as central ion by the bidentate amino dicarboxylic acid ligand to form a chelate complex. Depending on the central ion and amino dicarboxylic acid ligand, varying amounts of water may be bound, normally up to about 10 molecules per metal cation. The hydrohalide results through protonation of the amino group of the amino dicarboxylic acid ligand, the counter ion which is bound being a halide ion such as fluoride, chloride, bromide or iodide.

In a preferred embodiment of the present invention, M in the above formula (I) is magnesium, calcium or iron, n is 1 or 2, Hal is chlorine and m is 0, 1, 2 or 3. The compound of the formula (I) is in a particularly preferred embodiment an alkaline earth metal L-aspartate hydrohalide or an alkaline earth metal L-glutamate hydrohalide, in particular magnesium L-aspartate hydrochloride or magnesium L-glutamate hydrochloride, or a hydrate thereof. The use of magnesium L-aspartate hydrochloride in particular in the process according to the invention results in an excellently processable product having a specifically coarse structure and a narrow particle size distribution.

In the process according to the invention, it is essential for achieving the advantageous coarse structure of the hydrohalide of the complex compound that the air inlet temperature and the air outlet temperature in the spray-drying step (b) are controlled in a targeted manner in combination with a suitable spraying pressure in order to obtain granules with a specifically narrow particle size distribution, good flow and dissolving properties and a reduced hygroscopicity. It has surprisingly been found that with an air inlet temperature in a range from 300 to 350° C. and with an air outlet temperature in a range from 100 to 140° C. it is possible to obtain a stable granular product with excellent further processability when the aqueous solution is sprayed or atomized with a spraying pressure in a range from about 3 to about 5 bar. The exact temperature within these ranges depends on the hydrohalide to be subjected to the spray drying. However, a skilled person is capable of accurate setting within the above ranges. It is furthermore surprising in this connection that, despite the use of a comparatively high air inlet temperature, a coarse product is obtained.

The aqueous solution in step (a) can be sprayed or atomized into the top or bottom of a spray-drying tower. The gas used for drying, preferably air, can be passed cocurrently or countercurrently to the sprayed aqueous solution. However, it is preferred for the sprayed aqueous solution, which is atomized to fine droplets, to be sprayed into the top of a spray-drying tower, and for the gas used for drying to be passed cocurrently thereto, i.e. from the top to the bottom. Subsequent to the air outlet it is possible to provide a cyclone and/or a filter in order to separate a fine powdery material.

The spraying pressure in step (b) of the process according to the invention is in a range from about 3 bar to about 5 bar. The spraying pressure corresponds to the liquid inlet pressure of the nozzles. The atomization of the solution prepared in step (a) normally takes place through a single fluid nozzle or hollow cone nozzle which generates a hollow cone of liquid at the outlet from the nozzle, resulting in uniform droplets with a narrow droplet size distribution.

In a preferred embodiment of the process according to the invention, the freshly sprayed particles pass immediately after the spray-drying step through a fluidized bed in order for example to reduce the residual moisture. When the freshly sprayed particles impinge on the fluidized bed particles there is formation of a granular product according to the invention with excellent properties, which is subsequently discharged from the spray tower, preferably over a weir. A further possibility is to provide a subsequent sieving step. It is particularly preferred to provide a spray tower with integrated fluidized bed. The air inlet temperature to the fluidized bed is preferably in a range from 110 to 130° C., with the temperature of the product in the fluidized bed preferably being adjusted to about 100 to 125° C. The height of the fluidized bed is not in principle subject to special restrictions but is preferably set at from 15 cm to 30 cm. The setting of the holdup time of the product in the spray drier is within the routine judgement of a skilled person and can be determined in particular by adjusting the height of the wheel and the material throughput. The material throughput in the spray-drying step is in a range from 50 kg to 200 kg per hour, a preferred throughput being from 70 kg to 130 kg per hour. The volume of the spray drier is subject to no particular restrictions. However, it is preferably in a range from about 5 to 20 m$^3$, with a volume of about 8 m$^3$ being used most often for economic reasons.

A product with a very favourable apparent volume can be achieved in the process according to the invention for preparing the granular hydrohalide of the complex compound of relevance here. The apparent volume [volume of the uncompressed product (ml)/100 g of the product] is preferably in a range from 150 to 180 ml/100 g, with a particularly preferred apparent volume being about 170 ml/100 g.

The concentration of the aqueous solution in step (a) is subject in principle to no particular restrictions. However, it is preferred to adjust the concentration of the aqueous solution in step (a) to from 0.5 to 3 mol/l, preferably 1 mol/l to 2 mol/l, particularly preferably to about 1.3 mol/l to 1.5 mol/l.

The present invention further relates to the granules of a hydrohalide of a complex compound which is composed of a divalent metal cation as central ion and of an amino dicarboxylic acid ion and, where appropriate, water as ligand, where ≦10% of the particles have a particle size of <50 µm and ≦10% of the particles have a particle size of >400 µm, obtained by the process according to the invention described above.

It is particularly preferred for ≧70%, even more preferred ≧80%, of the particles, with preference ≧85% of the particles, of the granules to have a particle size in a range from about 100 µm to about 315 µm. It is further particularly preferred for ≧50% of the particles, with preference ≧55% of the particles, of the granules to have a particle size in a range from about 140 µm to about 250 µm. As stated above, the apparent volume [volume of the uncompressed product (ml)/100 g of the product] of such granules is preferably in a range from 150 to 180 ml/100 g, with a particularly preferred apparent volume being about 170 ml/100 g.

The present invention additionally relates to the use of the granules, prepared by the process according to the invention, of a hydrohalide of a magnesium-containing complex compound in magnesium therapy and as addition to animal feed. The granules obtained according to the invention of such hydrohalides of the magnesium complex compounds of relevance here are valuable pharmaceuticals and additions to animal feed. Thus, for example, magnesium L-aspartate hydrochloride is employed for targeted magnesium therapy and also as addition to animal feed and also as mineral supplement for productive livestock. The compounds can be employed in solid granular form or in aqueous solution.

The following examples are indicated in order to explain the invention in more detail without restricting it thereby.

EXAMPLES

Example 1

Preparation of Magnesium L-Aspartate Hydrochloride 836 kg of L-aspartic acid are added with stirring to 1753 l of demineralized water. 130 kg of magnesium oxide as powder are added to the resulting dispersion, and the mixture is heated to 60° C. with stirring. Then, while stirring, 628 g of magnesium chloride ($MgCl_2.6H_2O$) are added, and the mixture is heated with stirring at 60° C. for 2 h. The solution is subsequently filtered at 60° C. and spray dried with an air inlet temperature of about 320° C. and an air outlet temperature of about 120° C. with a spraying pressure of about 4 bar in a Niro spray drier.

The final product obtained is a magnesium L-aspartate hydrochloride having the following particle size distribution: <100 µm (6.19%), 100-140 µm (19.48%), 140-250 µm (57.84%), 250-315 µm (10.81%), 315-400 µm (4.78%) and 400-500 µm (0.90%). The apparent volume of this final product was 170ml/100 g.

Example 2

Preparation of Magnesium L-glutamate Hydrochloride 936 l of demineralized water are heated to 60° C., after which 484 kg of L-glutamic acid are added with stirring. 67 kg of magnesium oxide are added as powder in portions to the resulting dispersion while stirring continuously. The temperature rises, and the solution becomes clear after about 1 h. A solution of 480 kg of magnesium bromide hexahydrate and 384 l of water (35% strength solution) is added to this solution. The concentration of the complex is adjusted to 30% by using water. The solution is filtered and then spray dried under the conditions described in Example 1.

This results in magnesium L-glutamate hydrochloride as a white powder in 100% yield.

Example 3

Preparation of Calcium L-aspartate Hydrochloride 1010 l of demineralized water are heated to 60° C., after which 509 kg of L-aspartic acid are added while stirring. 142 kg of calcium hydroxide are added in the form of a powder in portions to the resulting dispersion while stirring continuously. The temperature rises further and the solution becomes clear after about 1 h. A solution of 281 kg of calcium chloride dihydrate in 325 l of water (35% strength solution) is added to this solution. The concentration based on the complex is adjusted to 30% with water. This is followed by filtration and spray drying in the manner described in Example 1.

This results in calcium L-aspartate hydrochloride in the form of a white powder in 100% yield.

Example 4

Preparation of Zinc L-aspartate Hydrochloride 1025 l of demineralized water are heated to 60° C., after which 464 kg of L-aspartic acid are added while stirring. 142 kg of zinc oxide in the form of a powder are added in portions to the resulting dispersion with continuous stirring. The temperature rises somewhat, but the solution does not become clear. The temperature is therefore raised to about 90° C., after which a clear solution is obtained. The concentration is adjusted to 30% by adding water.

A solution of 238 kg of zinc chloride in 441 l of water (35% strength solution) is added to the resulting solution. The concentration based on the complex is adjusted to 30% with water. This is followed by filtration and spray drying in the manner described in Example 1. This results in zinc L-aspartate hydrochloride in the form of a white powder in 100% yield.

Example 5

Preparation of Magnesium L-aspartate Hydrochloride 541 kg of L-aspartic acid are dispersed in 1016 l of demineralized water by stirring with heating to 60° C. 592 kg of a 25% by weight hydrochloric acid and then 164 kg of magnesium oxide as powder are added to this dispersion and stirred. After a clear solution has been obtained, it is filtered and spray dried in the manner described in Example 1, resulting in magnesium L-aspartate hydrochloride in the form of a white powder in 100% yield.

Example 6

Particle Size Distribution

The particle size distribution of granular magnesium L-aspartate hydrochloride prepared by the process according to the invention was compared with a finely powdered magnesium L-aspartate hydrochloride prepared by a standard process (disclosed in DE 32 38 118 A1). The comparative sieve analyses were performed using a Hosokawa Alpine air jet sieve, and the results are shown in Tables 1 and 2 below.

TABLE 1

| | | (standard process) | | | | | | | | |
|---|---|---|---|---|---|---|---|---|---|---|
| No. | Sieve (µm) | q (%-B) | Q (%-D) | 1 − Q (%-R) | Tare (g) | Gross (g) | Net (g) | p (kPa) | $t_{spec}$ | $t_{act}$ |
| 0 | 0 (receiver) | 55.4 | 0.0 | 100.0 | 0 | 50.0 | 50.0 | | 0 | |
| 1 | 63.0 | 23.8 | 55.4 | 44.6 | 0 | 22.3 | 22.3 | 5.35 | 180 | 180 |
| 2 | 90.0 | 15.6 | 79.2 | 20.8 | 0 | 10.4 | 10.4 | 4.87 | 180 | 180 |
| 3 | 150.0 | 5.2 | 94.8 | 5.2 | 0 | 2.6 | 2.6 | 5.50 | 120 | 120 |

The minimum particle size ($d_{min}$) was 0.7 µm, the maximum particle size ($d_{max}$) was 260.0 µm and the average particle size ($d_{50}$) was 54.9 µm. FIG. 1 shows the graphical representation of the particle size distribution of finely powdered magnesium L-aspartate hydrochloride prepared by a standard process disclosed in DE 32 38 118 A1.

TABLE 2

(process according to the present invention)

| No. | Sieve (µm) | q (%-B) | Q (%-D) | 1 − Q (%-R) | Tare (g) | Gross (g) | Net (g) | p (kPa) | $t_{spec}$ | $t_{act}$ |
|---|---|---|---|---|---|---|---|---|---|---|
| 0 | 0 (receiver) | 0.2 | 0.0 | 100.0 | 0 | 50.0 | 50.0 | | 0 | |
| 1 | 63.0 | 0.6 | 0.2 | 99.8 | 0 | 49.9 | 49.9 | 7.11 | 180 | 180 |
| 2 | 90.0 | 10.2 | 0.8 | 99.2 | 0 | 49.6 | 49.6 | 7.12 | 180 | 180 |
| 3 | 150.0 | 61.4 | 11.0 | 89.0 | 0 | 44.5 | 44.5 | 6.19 | 120 | 120 |
| 4 | 212.0 | 18.4 | 72.4 | 27.6 | 0 | 13.8 | 13.8 | 7.20 | 120 | 120 |
| 5 | 315.0 | 5.4 | 90.8 | 9.2 | 0 | 4.6 | 4.6 | 7.20 | 120 | 120 |
| 6 | 400.0 | 3.0 | 96.2 | 3.8 | 0 | 1.9 | 1.9 | 7.20 | 120 | 120 |
| 7 | 500.0 | 0.8 | 99.2 | 0.8 | 0 | 0.4 | 0.4 | 7.20 | 60 | 60 |

Figure 2:
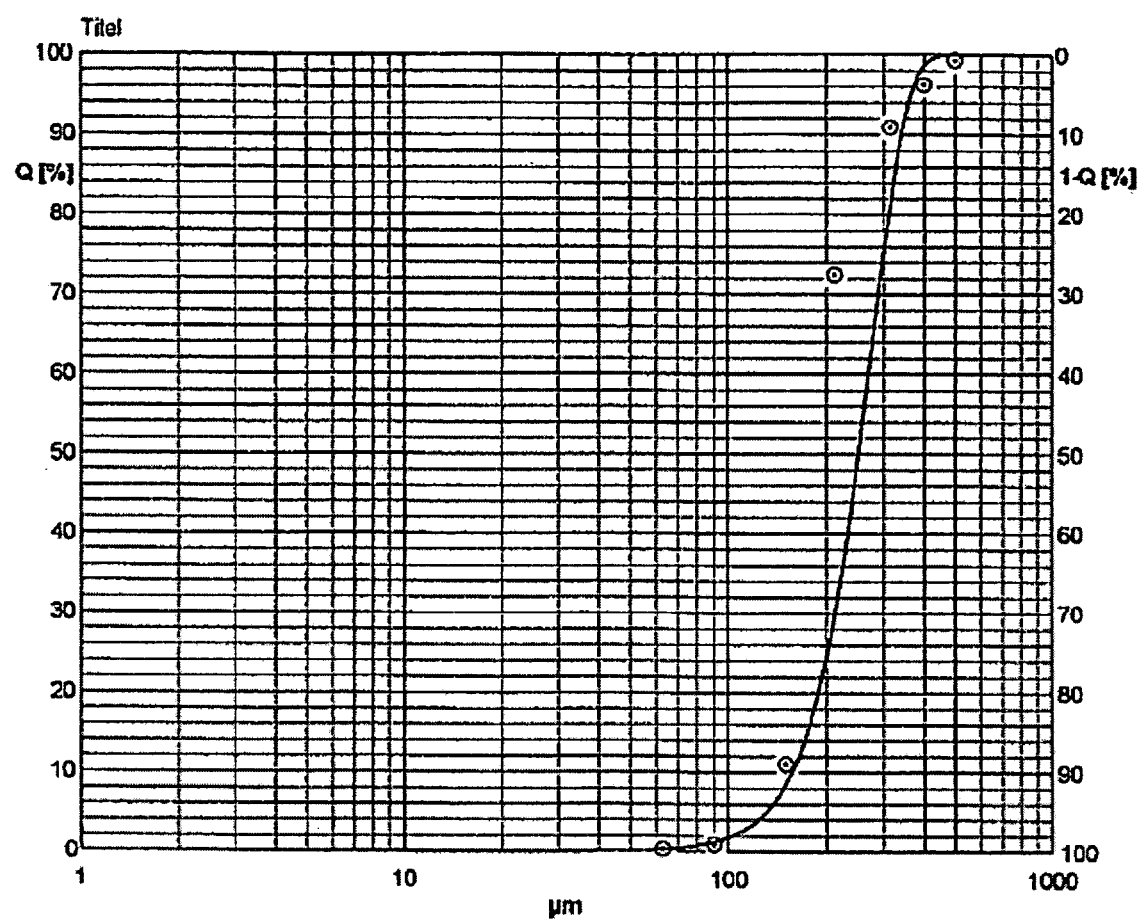
FIG. 2 is a graph showing the particle size distribution of granular magnesium L-aspartate hydrochloride prepared by the process according to the invention.

The minimum particle size ($d_{min}$) was 48.0 µm, the maximum particle size ($d_{max}$) was 448.7 µm and the average particle size ($d_{50}$) was 250.8 µm. FIG. 2 shows the graphical representation of the particle size distribution of granular magnesium L-aspartate hydrochloride prepared by the process according to the invention.

Example 7

Flow Time and Flowability

The flowability of granular magnesium L-aspartate hydrochloride prepared by the process according to the invention was compared with a finely powdered magnesium L-aspartate hydrochloride prepared by a standard process (disclosed in DE 32 38 118 A1). The test arrangement consisted of a conical flow funnel with a height of 22.5 cm, an upper internal diameter of 7.3 cm and a lower internal diameter of 8.2 mm. The test was carried out by the 2.9.16 Method, Ph. Eur., 4$^{th}$ edition, main volume 2002, as follows. 100 g portions of material were put into the funnel. Opening of the funnel orifice was followed by assessment of the flowability, and the time for the whole sample to flow out of the funnel was determined. Two samples were measured in each case. The results are shown in Table 3 below.

TABLE 3

(flowability)

| Preparation process | Standard | Standard | According to the invention | According to the invention |
|---|---|---|---|---|
| Flowability | uneven, not free-flowing | uneven, not free-flowing | free flowing | free flowing |
| Flow time | Cannot be determined | cannot be determined | 10 sec | 10 sec |

Example 8

Dissolving Properties

The dissolving properties of granular magnesium L-aspartate hydrochloride prepared by the process according to the invention were compared with a finely powdered magnesium L-aspartate hydrochloride prepared by a standard process (disclosed in DE 32 38 118 A1). The test arrangement consisted of a glass beaker with stirring bar which was adjusted to 20 revolutions per min. 250 ml of water were introduced and then 10 g of test material were added with the stirrer motor running. The time until dissolution was complete was measured. The results are shown in Table 4 below.

TABLE 4

(dissolving properties)

| Preparation process | Standard | Standard | According to the invention | According to the invention |
|---|---|---|---|---|
| Dissolving time | 7 min | 7 min | 3 min | 2 min |

Example 9

Water Uptake Capacity or Hygroscopicity

Figure 3:
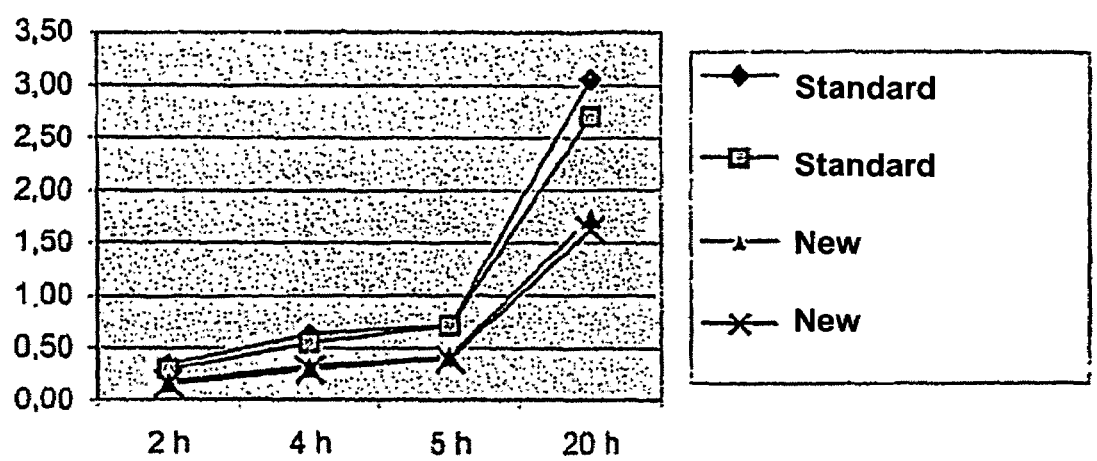
FIG. 3 a graphical representation of the measurements shown in Table 5.

The hygroscopicity of granular magnesium L-aspartate hydrochloride prepared by the process according to the invention was compared with a finely powdered magnesium L-aspartate hydrochloride prepared by a standard process (disclosed in DE 32 38 118 A1). The test arrangement consisted of a desiccator which was adjusted to a relative humidity of 75% with a saturated sodium chloride solution. In each case a defined amount of sample was weighed out and the sample dish was placed in the desiccator. The percentage increase in weight of the weighed amount was determined after 2, 4, 5 and 20 hours. The results are shown in Table 5 below, from which it is unambiguously evident that the hygroscopicity of the granules according to the invention is distinctly reduced compared with a finely powdered product according to the prior art. FIG. 3 shows a graphical representation of the measurements shown in Table 5.

TABLE 5

(hygroscopicity)

| Testing time | Standard | Standard | According to the invention | According to the invention |
|---|---|---|---|---|
| 2 h | 0.35 | 0.30 | 0.18 | 0.16 |
| 4 h | 0.63 | 0.55 | 0.33 | 0.30 |

TABLE 5-continued

| | (hygroscopicity) | | | |
|---|---|---|---|---|
| Testing time | Standard | Standard | According to the invention | According to the invention |
| 5 h | 0.72 | 0.71 | 0.43 | 0.40 |
| 20 h | 3.06 | 2.70 | 1.74 | 1.63 |

The invention claimed is:

1. Process for preparing a granular hydrohalide of a complex compound which is composed of a divalent metal cation as central ion and of an amino dicarboxylic acid ion and, where appropriate, water as ligand comprising the steps:
 (a) preparation of an aqueous solution of the hydrohalide of the complex compound,
 (b) spray drying of the aqueous solution obtained in step (a) at an air inlet temperature of from 300 to 350° C. and at an air outlet temperature of from 100 to 140° C. and with a spraying pressure of from 3 to 5 bar.

2. Process according to claim 1, wherein freshly sprayed particles obtained from step (b) are passed through a fluidized bed to reduce residual moisture, and are subjected where appropriate subsequently to a sieving step.

3. Process according to claim 1, wherein the hydrohalide of the complex compound is prepared by reacting an amino dicarboxylic acid with a hydroxide, oxide and/or carbonate of the divalent metal in aqueous solution and further reaction of the resulting aqueous solution or suspension with a halide of the divalent metal and/or hydrohalic acid.

4. Process according to claim 1, wherein the hydrohalide of the complex compound is a compound shown in formula (I) below:

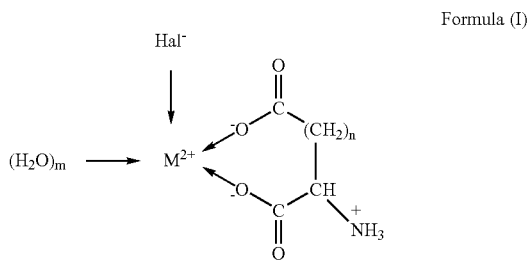

Formula (I)

in which $M^{2+}$ is the divalent metal cation, $Hal^-$ is a halide ion, n is 1 or 2 and m is 0 to 10.

5. Process according to claim 1, wherein the amino dicarboxylic acid is L-glutamic acid or L-aspartic acid.

6. Process according to claim 1, wherein the divalent metal is an alkaline earth metal or a heavy metal.

7. Process according to claim 1, wherein the hydrohalide of the complex compound is an alkaline earth metal L-aspartate hydrohalide or an alkaline earth metal L-glutamate hydrohalide.

8. Process according to claim 1, wherein the hydrohalide of the complex compound is magnesium L-aspartate hydrochloride or magnesium L-glutamate hydrochloride.

9. Process according to claim 1, wherein the concentration of the aqueous solution in step (a) is set at from 0.5 mol/l to 3 mol/l.

10. Process for preparing a granular hydrohalide of a complex compound which is composed of a divalent metal cation as central ion and of an amino dicarboxylic acid ion and, where appropriate, water as ligand comprising the steps:
 (a) preparation of an aqueous solution of the hydrohalide of the complex compound, by reacting an amino dicarboxylic acid with a hydroxide, oxide and/or carbonate of the divalent metal in aqueous solution and further reaction of the resulting aqueous solution or suspension with a halide of the divalent metal and/or hydrohalic acid;
 (b) spray drying of the aqueous solution obtained in step (a) at an air inlet temperature of from 300 to 350° C. and at an air outlet temperature of from 100 to 140° C. and with a spraying pressure of from 3 to 5 bar, and
 wherein the freshly sprayed particles after step (b) are passed through a fluidized bed to reduce the residual moisture, and are subjected where appropriate subsequently to a sieving step.

11. Process according to claim 10, wherein the hydrohalide of the complex compound is a compound shown in formula (I) below:

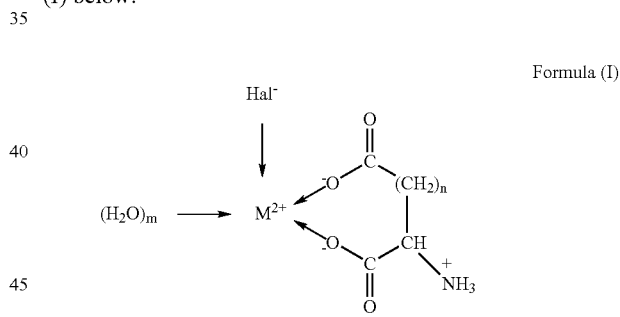

Formula (I)

in which $M^{2+}$ is the divalent metal cation, $Hal^-$ is a halide ion, n is 1 or 2 and m is 0 to 10.

* * * * *